US00PP09086P

United States Patent [19]

Mantel

[11] Patent Number: Plant 9,086

[45] Date of Patent: Mar. 21, 1995

[54] LILIUM "TICINO"

[76] Inventor: Homme Mantel, P.O. Box 1314, Sandy, Oreg. 97055

[21] Appl. No.: 280,201

[22] Filed: Jul. 25, 1994

[51] Int. Cl.[6] ..... A01H 5/00
[52] U.S. Cl. ..... Plt./87.4
[58] Field of Search ..... Plt. 87.4

*Primary Examiner*—James R. Feyrer

[57] ABSTRACT

A new variety of hybrid lily plant bearing upfacing flowers of excellent form and long persistence, both on the plant and as cut-flowers. The new hybrid is particularly characterized by its elongate racemose inflorescence with may secondary buds, all borne on ascending pedicels, and by its non-fading deep red flowers which recurve only slightly at the tips even after the flowers age. This combination is completely new in the Asiatic hybrid divisions of lilies suited to forcing and to mass commercial cultivation. The variety is resistant to fusarium disease and shows tolerance of virus. The bulbs may be precooled and forced for cut-flower production. The clone is vigorous and is a good grower and propagator.

1 Drawing Sheet

BACKGROUND OF THE INVENTION

My new variety of lily plant originated as a seedling which first flowered in 1989 in 't Zandt, the Netherlands. The breeding efforts had as their objective the production of Asiatic hybrid lilies with upfacing, non-fading, deep red flowers, suited to forcing into flower out of season, heretofore unknown in the lily breeding art.

I achieved the desired objective by pollinating an upfacing medium red Asiatic unnamed seedling with a tall, deep red outfacing Asiatic unnamed seedling. Both parents were produced by me and never released. The seed parent for 'Ticino' was a seedling from 'Sunkissed' (unpatented)×'Red Carpet' (unpatented). 'Sunkissed' and 'Red Carpet' were commercially available as garden lilies during the 1970's. The pollen parent for 'Tyrolia' was produced from 'Chinook' (unpatented)×-'Burgandy' strain (unpatented). 'Chinook' was grown commercially in the United States and the Netherlands as a garden lily and cut-flower variety during the 1970's and 1980's; 'Burgandy' strain was grown commercially in the United States as a garden lily.

The flowers of my new lily are characterized by upfacing, broad-tepalled form and by deep, non-fading red coloration. The flowers recurve only slightly at the tips, even in the oldest flowers; and they are borne on an elongate racemose inflorescence with an exceptionally large bud count and with many secondary buds (on the lower buds). In addition, the clone possesses to a high degree desirable characteristics of hybrid vigor. The clone is a good grower and propagator, as observed at 't Zandt, the Netherlands.

My new variety of lily plant has been asexually reproduced by me and under my direction at 't Zandt, the Netherlands. Successive generations produced by natural propagation from bulbets, by bulb scale propagation, and by tissue culturing from bulb scale explants have demonstrated that the novel and distinctive characteristics of my new variety are fixed and hold true under asexual propagation from generation to generation.

DESCRIPTION OF THE DRAWING

My new variety of lily plant is illustrated in the accompanying photographic drawing, which shows the open bloom in full color and illustrates the unusually elongate racemose inflorescence with its many secondary buds and its dark, ascending pedicels, and in particular the novel and distinctive non-fading flowers which recurve only slightly at the tips, even in the oldest flowers.

DESCRIPTION OF THE NEW VARIETY

The following is a detailed description of my new variety of Asiatic hybrid lily, with nomenclature according to the *International Lily Register* (Royal Horticultural Society of London, Second Edition, 1969), and with color designations according to the Colour Chart of The Royal Horticultural Society, published by the Society in 1966.

The Plant

Origin: Seedling.

*Seed parent.*—Unnamed upfacing red Asiatic seedling.

*Pollen parent.*—Unnamed outfacing red Asiatic seedling.

Commercial classification: Hybrid Lilium clone.

Horticultural classification: Division I-A, Upfacing Asiatic Hybrid Lily, according to the Horticultural Classification of Lilies, Royal Horticultural Society of London.

Form: Single stem, erect and stately.

Height: 1.25 to 1.75 m from bulbs 12 to 16 cm in circumference, provided their light levels are adequate; low light levels may cause "stretching."

Growth: Vigorous and upright.

Foliage quantity: Abundant.

Size of leaf: 7 to 12 cm long, 2 to 4 cm wide.

Shape of leaf: Lanceolate (pointed).

Texture: Leathery and glossy.

Color: Very dark green, lighter on lower side.

Bulb:

*Size.*—Any size, ranging to 25 cm circumference commercially.

*Color.*—White, with flushes of pink or yellow after exposure to light.

The Bud

Form: Obtuse, ovoid, and long.

Size: 7 to 10 cm long and 7 to 12 cm in circumference just prior to opening.

Opening: Bud opens slowly, in response to morning light; this takes about one hour.

Color: Deep red, RHS CC Red 53 B just prior to opening. Buds are moderately pubescent, particularly along the midribs; hairs are short and colorless.

Peduncle: Averages 5 to 10 cm, but it may elongate if light levels are too low, if bulbs have been improperly stored prior to forcing, or if bulbs are very large, producing an unusually large inflorescence. Color is deep plum over green, appearing almost black to the eye. Axils are noticeably pubescent.

The Flower

Blooming habit: Annually in midseason; flowers once and profusely.

Size: Flowers are large, averaging 14 to 17 cm in diameter, recurving only slightly at the tips on the second or third day to 12 to 16 cm in diameter. Inner tepals average 3 cm wide; outer tepals average 2.5 to 3 cm wide.

Borne: In a single racemic inflorescence producing 8 to 20 flowers from a bulb 12 to 16 cm in circumference.

Shape: Broad-tepalled and recurving only very slightly at the tips, creating a "flat face."

Tepalage: Typical of genus Lilium, with 6 imbricated tepals.

Tepal:

*Color.*—Deep, non-fading red, basically RHS CC Red 53 A-B. A slightly more purple red (RHS CC Red-Purple 60 B-C) is carried in the upper epidermis, over the more scarlet red that is found in the middle cell layers. As the flowers age, they may appear slightly more purple-red, but the color remains intense and does not fade. In cool weather, flowers may also appear slightly more purple-red, but in this case the color will appear more rather than less intense.

*Spotting.*—Flowers are virtually spotless; they occasionally bear inconspicuous small deep magenta-red papillae at the tepal bases.

*Longevity.*—Tepals stay on stems about four weeks.

Nectaries: Nectaries are generally deep red, inconspicuous, and lightly pubescent, with short white to red hairs noticeable only when the flower is completely open.

Pedicel: *Length.*—Average 7 to 10 cm long, ascending. Lower pedicels generally have secondary buds with pedicels 4 to 6 cm long.

*Color.*—Dark green with deep plum overlay; appear almost black to the eye.

*Form.*—Sturdy and ascending, exceptionally strong. Leaf axil at base of each pedicel is pubescent with white to colorless hairs.

Color changes: Flowers become slightly more purple-red as flower ages or when temperatures are very cool.

Appearance: Flower is shiny.

Disease resistance: The flower and plant are resistant to disease; in particular, they are resistant to Fusarium bulb rot and Botrytis blight.

Fragrance: None.

Lasting quality: The flower is long lasting, both on the plant and as a cut-flower.

The Reproductive Organs

Stamens: Arrangement typical of genus Lilium. Six stamens with soft red-purple (RHS CC Red-Purple 60C) filaments 8–10 cm long.

Pollen and anthers (dehisced): RHS CC Greyed-Red 179 A to 178 C.

Pistil: One in number, deep red-purple (RHS CC Red-Purple 59B-C), 6 to 8 cm long.

Stigma: Deep red-purple (RHS CC Red-purple 59 A to Greyed Purple 187 A-B), large in size.

Characteristics of ovary: Characteristic of genus Lilium.

The Fruit

Fertility: The fruit bears a fertile seed.

Shape: Ovoid.

Color at maturity: Soft brown, overlaid with soft plum.

My new variety of Asiatic hybrid lily most nearly resembles 'Redsong' (U.S. Plant Pat. No. 6,375), but it is taller, with a higher bud count, a much more elongate racemost inflorescence, and with flowers of a more intense and slightly more magenta red. It also produces many secondary buds.

I claim:

1. A new and distinctive variety of Asiatic hybrid lily plant substantially as herein shown and described, characterized by its high resistance to disease; its tolerance of virus; its vigorous growth and rapid natural propagation; the excellence of its flower form and substance; its versatility both as a garden plant and as a cut-flower produced from pre-cooled bulbs forced under glass out of season; and in particular by its unique upfacing, non-fading, deep red flowers, borne on an elongate racemose inflorescence with secondary buds, a combination unique among hybrid lilies suited to forcing and to mass commercial cultivation.

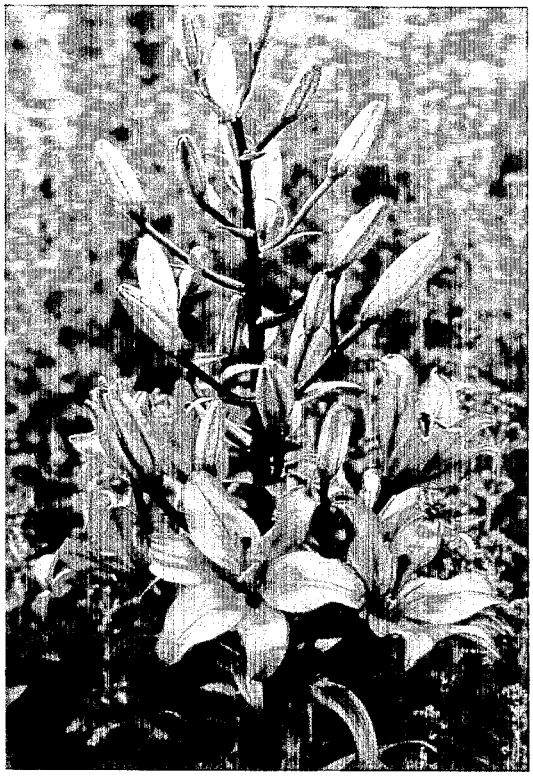

* * * * *